US012365609B2

(12) United States Patent
Foss et al.

(10) Patent No.: US 12,365,609 B2
(45) Date of Patent: *Jul. 22, 2025

(54) STERILE AND/OR PURIFIED FLUID AND/OR SOLUTION DELIVERY SYSTEM

(71) Applicants: THE CLEVELAND CLINIC FOUNDATION, Cleveland, OH (US); PARKER-HANNIFIN CORPORATION, Cleveland, OH (US)

(72) Inventors: Joseph Foss, Cleveland, OH (US); William Kolosi, Cleveland, OH (US); Dale Ashby, Cleveland, OH (US); Gino Banco, Cleveland, OH (US); Paul Resendes, Cleveland, OH (US)

(73) Assignees: THE CLEVELAND CLINIC FOUNDATION, Cleveland, OH (US); PARKER-HANNIFIN CORPORATION, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/654,819

(22) Filed: May 3, 2024

(65) Prior Publication Data

US 2024/0286938 A1    Aug. 29, 2024

Related U.S. Application Data

(60) Division of application No. 17/177,653, filed on Feb. 17, 2021, now Pat. No. 11,981,588, which is a
(Continued)

(51) Int. Cl.
*C02F 1/00* (2023.01)
*A61G 12/00* (2006.01)
(Continued)

(52) U.S. Cl.
CPC ............ *C02F 1/687* (2013.01); *A61G 12/001* (2013.01); *A61G 12/008* (2013.01);
(Continued)

(58) Field of Classification Search
CPC .. C02F 1/687; C02F 1/008; C02F 1/50; C02F 1/001; C02F 1/02; C02F 1/283;
(Continued)

(56) References Cited

U.S. PATENT DOCUMENTS 3,876,234 A    3/1975  Harms
4,022,205 A    5/1977  Tenczar
(Continued)

FOREIGN PATENT DOCUMENTS

EP    2447697 A1    5/2012
JP    S5980432 U    9/1983
(Continued)

OTHER PUBLICATIONS

European Office Action for corresponding European Application Serial No. 16712609.3, dated Oct. 29, 2021, pp. 1-4.
(Continued)

*Primary Examiner* — Akash K Varma
(74) *Attorney, Agent, or Firm* — Tarolli, Sundheim, Covell & Tummino LLP

(57) ABSTRACT

One aspect of the present disclosure can include a system for dispensing purified and sterilized fluid and/or solution. The delivery system can include a fluid reservoir, a sterilization and/or purification mechanism, a solution production mechanism, a dispensing mechanism, and a controller. The system can dispense the purified and sterilized fluid and/or solution on-demand.

8 Claims, 8 Drawing Sheets

Related U.S. Application Data continuation of application No. 15/555,612, filed as application No. PCT/US2016/022287 on Mar. 14, 2016, now Pat. No. 11,021,378.

(60) Provisional application No. 62/132,618, filed on Mar. 13, 2015, provisional application No. 62/132,589, filed on Mar. 13, 2015.

(51) Int. Cl.

| | | |
|---|---|---|
| *A61L 2/00* | (2006.01) | |
| *A61L 2/02* | (2006.01) | |
| *A61L 2/26* | (2006.01) | |
| *A61L 9/00* | (2006.01) | |
| *C02F 1/02* | (2023.01) | |
| *C02F 1/28* | (2023.01) | |
| *C02F 1/32* | (2023.01) | |
| *C02F 1/42* | (2023.01) | |
| *C02F 1/44* | (2023.01) | |
| *C02F 1/469* | (2023.01) | |
| *C02F 1/50* | (2023.01) | |
| *C02F 1/68* | (2023.01) | |
| *C02F 9/20* | (2023.01) | |
| *G01N 35/04* | (2006.01) | |
| *G01N 35/10* | (2006.01) | |
| *C02F 101/20* | (2006.01) | |
| *C02F 103/02* | (2006.01) | |

(52) U.S. Cl.
CPC ............. *A61L 2/0017* (2013.01); *A61L 2/022* (2013.01); *A61L 2/26* (2013.01); *A61L 9/00* (2013.01); *C02F 1/008* (2013.01); *C02F 1/50* (2013.01); *C02F 9/20* (2023.01); *A61L 2202/21* (2013.01); *C02F 1/001* (2013.01); *C02F 1/02* (2013.01); *C02F 1/283* (2013.01); *C02F 1/32* (2013.01); *C02F 1/42* (2013.01); *C02F 2001/427* (2013.01); *C02F 1/444* (2013.01); *C02F 1/4691* (2013.01); *C02F 1/68* (2013.01); *C02F 2101/20* (2013.01); *C02F 2103/026* (2013.01); *C02F 2201/006* (2013.01); *C02F 2201/008* (2013.01); *C02F 2209/006* (2013.01); *C02F 2209/02* (2013.01); *C02F 2209/03* (2013.01); *C02F 2209/05* (2013.01); *C02F 2209/06* (2013.01); *C02F 2209/40* (2013.01); *C02F 2301/043* (2013.01); *C02F 2303/04* (2013.01); *G01N 2035/0443* (2013.01); *G01N 35/1002* (2013.01)

(58) Field of Classification Search
CPC .... C02F 1/32; C02F 1/42; C02F 1/444; C02F 1/4691; C02F 1/68; C02F 1/325; C02F 1/4695; C02F 1/00; C02F 1/28; C02F 1/469; C02F 1/44; C02F 9/005; C02F 9/00; C02F 9/02; C02F 9/04; C02F 9/12; C02F 9/20; C02F 2001/427; C02F 2101/20; C02F 2103/026; C02F 2103/02; C02F 2201/008; C02F 2201/006; C02F 2209/006; C02F 2209/02; C02F 2209/03; C02F 2209/05; C02F 2209/06; C02F 2209/40; C02F 2303/04; C02F 2301/043; A61G 12/001; A61G 12/008; A61G 12/00; A61L 2/0017; A61L 2/022; A61L 2/26; A61L 2/00; A61L 2/02; A61L 2/10; A61L 2202/21; A61L 9/00; G01N 35/1002; G01N 35/04; G01N 35/10; G01N 2035/0443; B01D 61/48; B01D 27/08; B01F 1/00; B01F 15/02; F16J 15/14
USPC .............................................. 210/739, 748.11
See application file for complete search history.

(56) References Cited

U.S. PATENT DOCUMENTS

| | | |
|---|---|---|
| 4,495,067 A | 1/1985 | Klein et al. |
| 5,032,265 A | 7/1991 | Jha et al. |
| 5,259,954 A | 11/1993 | Taylor |
| 5,919,357 A | 7/1999 | Wilkins et al. |
| 6,080,313 A | 6/2000 | Kelada |
| 6,139,571 A | 10/2000 | Fuller et al. |
| 6,164,314 A | 12/2000 | Saputo et al. |
| 6,302,864 B1 | 10/2001 | Nowosielski |
| 6,423,219 B1 | 7/2002 | Chandler |
| 7,017,953 B2 | 3/2006 | Benscoter et al. |
| 7,250,619 B2 | 7/2007 | Taylor et al. |
| 2002/0162778 A1* | 11/2002 | Peabody ............... A61M 1/28 210/85 |
| 2005/0171501 A1 | 8/2005 | Kelly |
| 2006/0169719 A1 | 8/2006 | Bui |
| 2006/0204405 A1 | 9/2006 | Tryggvason et al. |
| 2008/0146991 A1 | 6/2008 | Hernandez et al. |
| 2009/0182263 A1 | 7/2009 | Burbank et al. |
| 2009/0283409 A1 | 11/2009 | Stern et al. |
| 2009/0321339 A1 | 12/2009 | Suzuki et al. |
| 2010/0307973 A1* | 12/2010 | Grcevic ............... B01D 61/025 210/639 |
| 2011/0006790 A1 | 1/2011 | Kirkaune |
| 2011/0196319 A1 | 8/2011 | Arscott, II et al. |
| 2013/0224878 A1 | 8/2013 | Wilson et al. |
| 2014/0021115 A1 | 1/2014 | Ellegaard |
| 2014/0124430 A1 | 5/2014 | Herges et al. |

FOREIGN PATENT DOCUMENTS

| | | | |
|---|---|---|---|
| JP | 2002500068 | A | 1/2002 |
| JP | 2002538945 | A | 11/2002 |
| JP | 2007501061 | A | 1/2007 |
| JP | 2007521037 | A | 8/2007 |
| JP | 2007252396 | A | 10/2007 |
| JP | 2009028602 | A | 2/2009 |
| JP | 5242787 | B2 | 7/2013 |
| KR | 20030008504 | A | 1/2003 |
| KR | 1012191 | B1 | 2/2011 |
| WO | 9934840 | A1 | 7/1999 |
| WO | 2005012733 | A2 | 2/2005 |
| WO | 2005016094 | A1 | 2/2005 |
| WO | 2011055133 | A2 | 5/2011 |

OTHER PUBLICATIONS

European Examination Report for corresponding European Application Serial No. 16712609.3 mailed Mar. 11, 2021, pp. 1-4.
European Office Action for the corresponding European Application Serial No. 16712611.9, dated Dec. 21, 2020, pp. 1-12.
International Search Report corresponding to International App. No. PCT/US2016/022287, dated May 18, 2016, 5 pages.
Japanese Office Action for corresponding Japanese Application Serial No. JP 2017-547454, dated Oct. 31, 2019, pp. 1-4.
Korean Office Action for corresponding Korean Application Serial No. 2018-052816524, mailed Aug. 3, 2018, pp. 1-10.
Korean Office Action for corresponding Korean Application Serial No. 2018-052816670, mailed Aug. 3, 2018, pp. 1-14.
Korean Office Action for corresponding Korean Application Serial No. 10-2017-7025646, mailed Apr. 4, 2019, 3 pages.

* cited by examiner

STERILE AND/OR PURIFIED FLUID AND/OR SOLUTION DELIVERY SYSTEM

RELATED APPLICATIONS

This application is a divisional of U.S. patent application Ser. No. 17/177,653, filed Feb. 17, 2021, which is a continuation of U.S. patent application Ser. No. 15/555,612, filed Sep. 5, 2017, now U.S. Pat. No. 11,021,378, which is a 371 of PCT/US2016/022287, filed Mar. 14, 2016, which claims the benefit of U.S. Provisional Patent Application Ser. Nos. 62/132,618, filed Mar. 13, 2015, and 62/132,589, filed Mar. 13, 2015, the entirety of each of which is hereby incorporated by reference for all purposes.

TECHNICAL FIELD

The present disclosure relates to systems and methods for the production of a sterilized and/or purified fluid and/or solution and, more particularly, to a system for on-demand delivery of sterile and/or purified fluids and/or solutions.

BACKGROUND

The use of systems in the medical field is known. A system may be used to dispense purified water, sterilized water, a sodium chloride solution, or any other fluid that may be needed during a medical procedure (e.g., surgery). Conventional systems rely on one or more containers (generally bags) for the supply of sterile fluid. The storage and transport of the bags, however, can be cumbersome. Additionally, certain medical procedures often require a greater volume of sterile fluid than what can be provided via the bags.

SUMMARY

The present disclosure relates to systems and methods for the production of a sterilized and/or purified fluid and/or solution and, more particularly, to a system for on-demand delivery of sterile and/or purified fluids and/or solutions.

One aspect of the present disclosure can include a system for on-demand deliver of sterile and/or purified fluids and/or solutions. The system can comprise a housing and at least one fluid reservoir associated with the housing. The at least one fluid reservoir can be configured to hold a fluid. A sterilization and/or purification mechanism can be in fluid communication with the at least one fluid reservoir. The sterilization and/or purification mechanism can be configured to sterilize and purify the fluid held by the at least one fluid reservoir. A solution production mechanism can be in fluid communication with the sterilization and/or purification mechanism. The solution production mechanism can be configured to optionally mix a solute with the sterilized and/or purified fluid to produce a solution. A dispensing mechanism can be in fluid communication with the sterilization and/or purification mechanism and configured to dispense the fluid and/or the solution. A controller can be associated with one or more of the housing, the at least one fluid reservoir, the sterilization and/or purification mechanism, the solution production mechanism and the dispensing mechanism. The controller can be configured to modulate at least one operating characteristic of the system. The system can be configured to deliver the sterile and/or purified fluid and/or solution immediately after a request for fluid and/or solution is made by an operator.

Another aspect of the present disclosure can include a method for providing a sterile and/or purified fluid and/or solution. The method can include the following steps: (a) flowing fluid through at least one filter of a system to remove impurities from the fluid; (b) deionizing the fluid; (c) reducing microorganisms (e.g., bacteria) and/or endotoxins (e.g., bacterial endotoxins) in the fluid (e.g., as compared to an initial or baseline level of the microorganisms and/or endotoxins); (d) optionally creating a solution by mixing the fluid with a solute after steps (a)-(c); and (d) requesting that the fluid and/or solution be dispensed from the system such that fluid and/or solution is dispensed immediately after the request is made.

BRIEF DESCRIPTION OF THE DRAWINGS

The foregoing and other features and advantages of the present disclosure will become apparent to those skilled in the art to which the present disclosure relates upon reading the following description with reference to the accompanying drawings, in which.

DETAILED DESCRIPTION

Definitions

Figure 1:
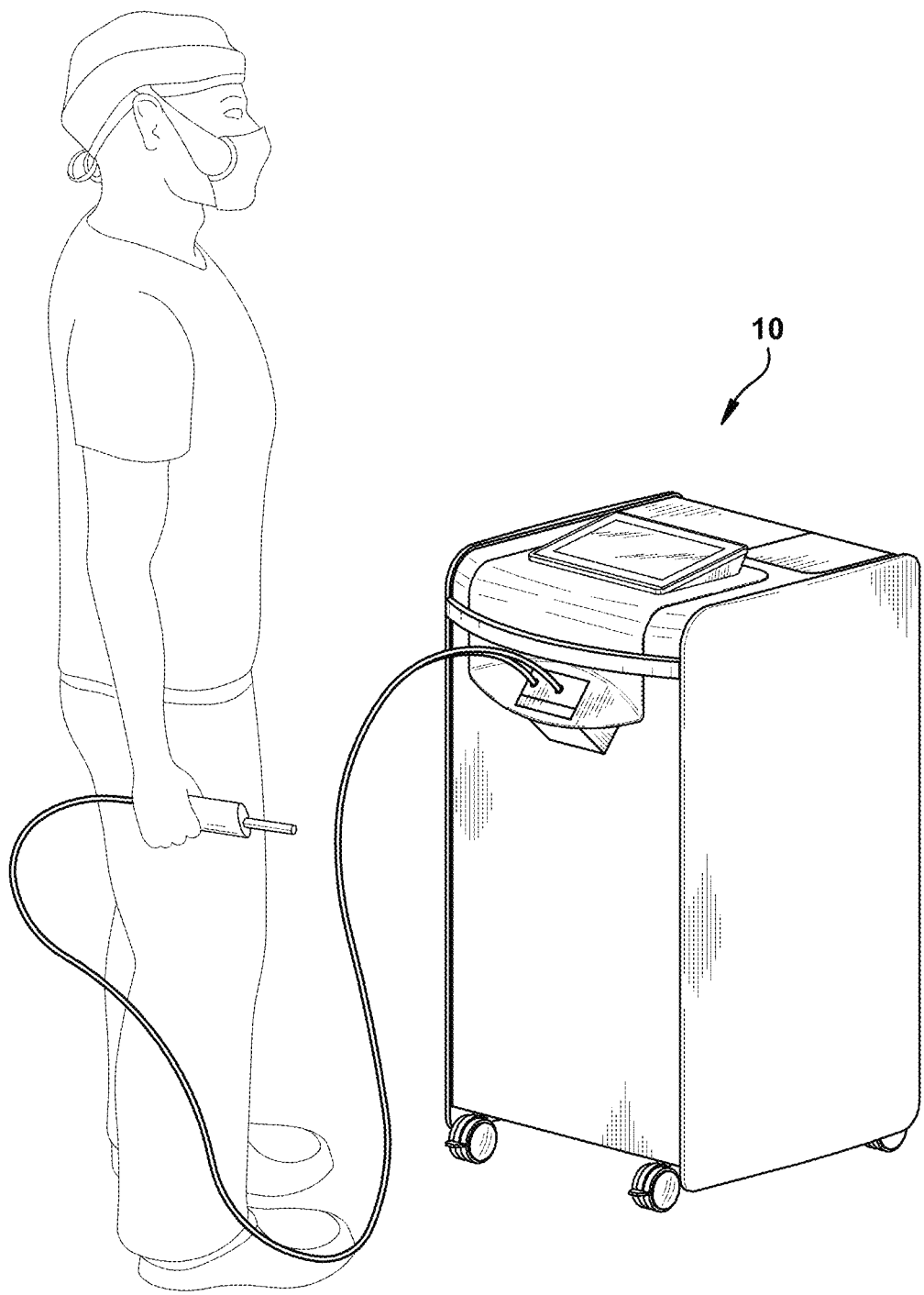
FIG. 1 is a perspective view showing a sterile and/or purified fluid and/or solution delivery system constructed in accordance with one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present.

In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another.

Thus, a "first" element discussed below could also be termed a "second" element without departing from the teachings of the present disclosure. The sequence of operations (or steps) is not limited to the order presented in the claims or figures unless specifically indicated otherwise.

Overview

The present disclosure relates to systems and methods for the production of a sterilized and/or purified fluid and/or solution and, more particularly, to a system for on-demand delivery of sterile and/or purified fluids and/or solutions. The present disclosure provides a convenient and economical way of dispensing a sterile and/or purified fluid and/or solution. Drawbacks associated with conventional sterile fluid delivery systems (e.g., reverse osmosis-based systems), include fluid supply limitations, and the need to store fluid bags associated with such systems. Additionally, reverse osmosis-based systems are only capable of supplying on-demand sterile fluid at extremely low flow rates. Advantageously, the systems and methods of the present disclosure are able to provide on-demand sterile and/or purified fluid and/or solution at a flow rate greater than such conventional systems. Other advantages of the present disclosure are discussed below. In particular, it has been found that certain configurations of the present disclosure have been unexpectedly found to produce sterile and/or purified water that conforms to United States Pharmacopeial standards for water for injection and has less than 0.5 mg/L of total organic carbon, less than 1.3µ s/c, @ 25° C., less than 0.25 EU/mL endotoxins, and less that 10 CFU/100 mL microbial count.

Systems

Figure 2:
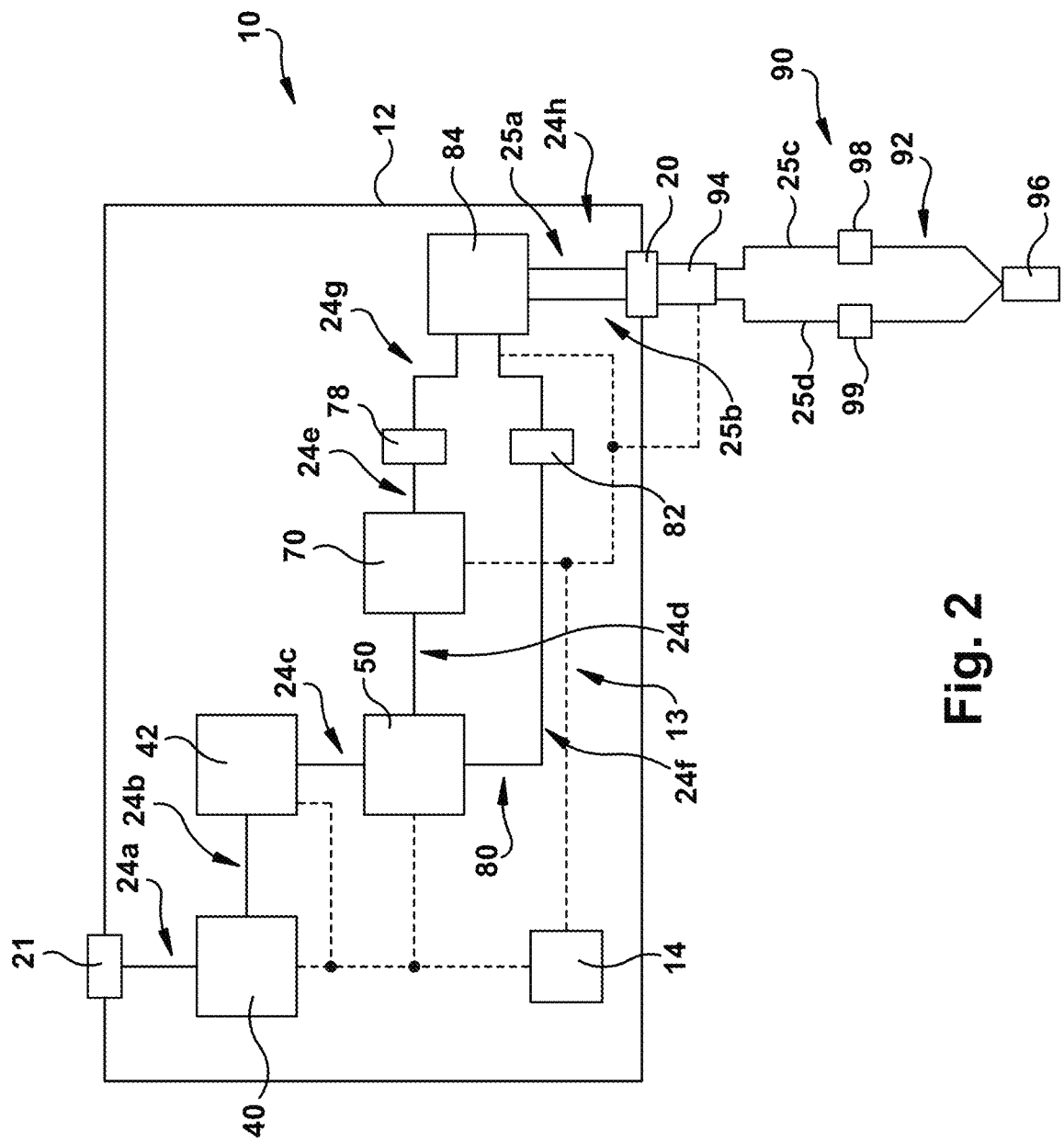
FIG. 2 is a schematic illustration of the system in FIG. 1.

One aspect of the present disclosure can include a system 10 (FIGS. 1-2) for on-demand delivery of a sterile and/or purified fluid and/or solution. As shown in FIG. 2, the system 10 can comprise a housing 12 and at least one fluid reservoir 40 associated with the housing 12. The at least one fluid reservoir 40 can be configured to hold a fluid. Alternatively, the reservoir 40 can be omitted, and the system 10 can be permanently attached to an external fluid source (e.g., a faucet). A sterilization and/or purification mechanism 50 can be in fluid communication with the at least one fluid reservoir 40. The sterilization and/or purification mechanism 50 can be configured to sterilize and purify the fluid held by the at least one fluid reservoir 40. A solution production mechanism 70 can be in fluid communication with the sterilization and/or purification mechanism 50. The solution production mechanism 70 can be configured to optionally mix a solute with the sterilized and/or purified fluid to produce a solution. A dispensing mechanism 90 can be in fluid communication with the sterilization and/or purification mechanism 50 and configured to dispense the fluid and/or the solution. A controller 14 can be associated with one or more of the housing 12, the at least one fluid reservoir 40, the sterilization and/or purification mechanism 50, the solution production mechanism 70 and the dispensing mechanism 90 via electronic signals 13. The controller 14 can be configured to modulate at least one operating characteristic of the system 10.

The system 10 can be configured to deliver the sterile and/or purified fluid and/or solution immediately after a request for fluid and/or solution is made by an operator. As used herein, the terms "on-demand" and "instantaneously" can mean that, after an initial start-up time period (e.g., five minutes or less), the systems and methods of the present disclosure can supply sterile and/or purified fluids and/or solutions within about ten seconds after a request for the sterile and/or purified fluid and/or solution has been made.

In one aspect, the housing 12 can be configured to enclose certain components of the system 10, such as the fluid reservoir 40, the sterilization and/or purification mechanism 50, and the solution production mechanism 70. The housing 12 can include a plurality of walls that define an interior storage space for certain components of the system 10. One or more of the walls can be opaque or transparent. In one aspect, the walls of the housing 12 can be arranged to have a cuboid configuration that occupies approximately 0.5 cubic meters of space. It will be appreciated that the housing 12 can be arranged to have any other suitable shape that allows the housing 12 to enclose components of the system 10. The housing 12 can be made of one or a combination of materials, such as metals (e.g. stainless steel) or non-metals (e.g. hardened plastics). The housing 12 can be provided with wheels 16 to facilitate transportation of the system 10. The housing 12 can be provided with one or more doors for accessing components of the system 10. In one aspect, a door 18 can be configured to gain access to components of the solution production mechanism 70, such as a multi-bore solute cartridge carrier 72 (discussed below). An additional door (not shown) can be configured to gain access to filtration components.

Figure 5:
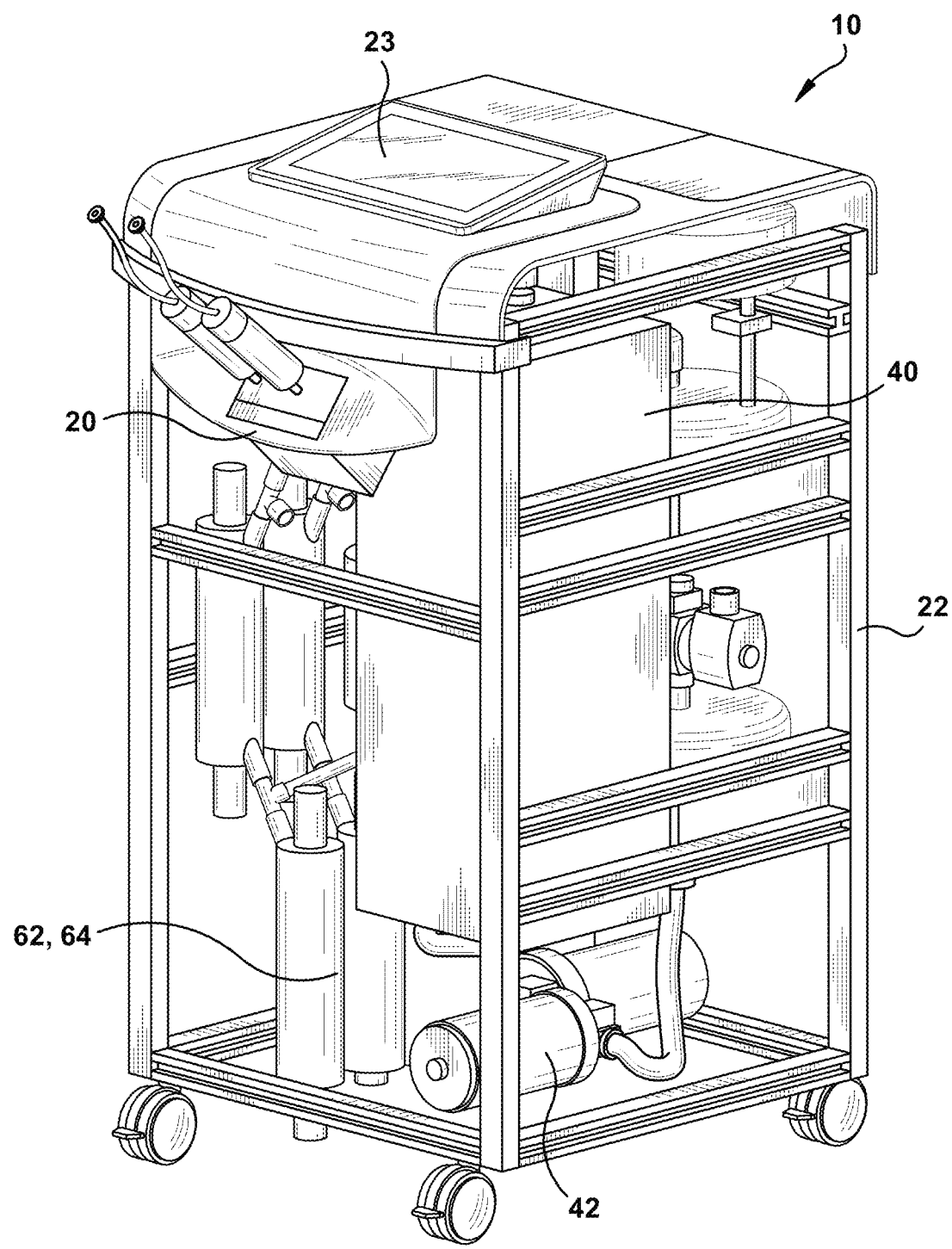
FIG. 5 is a perspective view of the system in FIG. 1 with portions of its housing removed.
Figure 6:
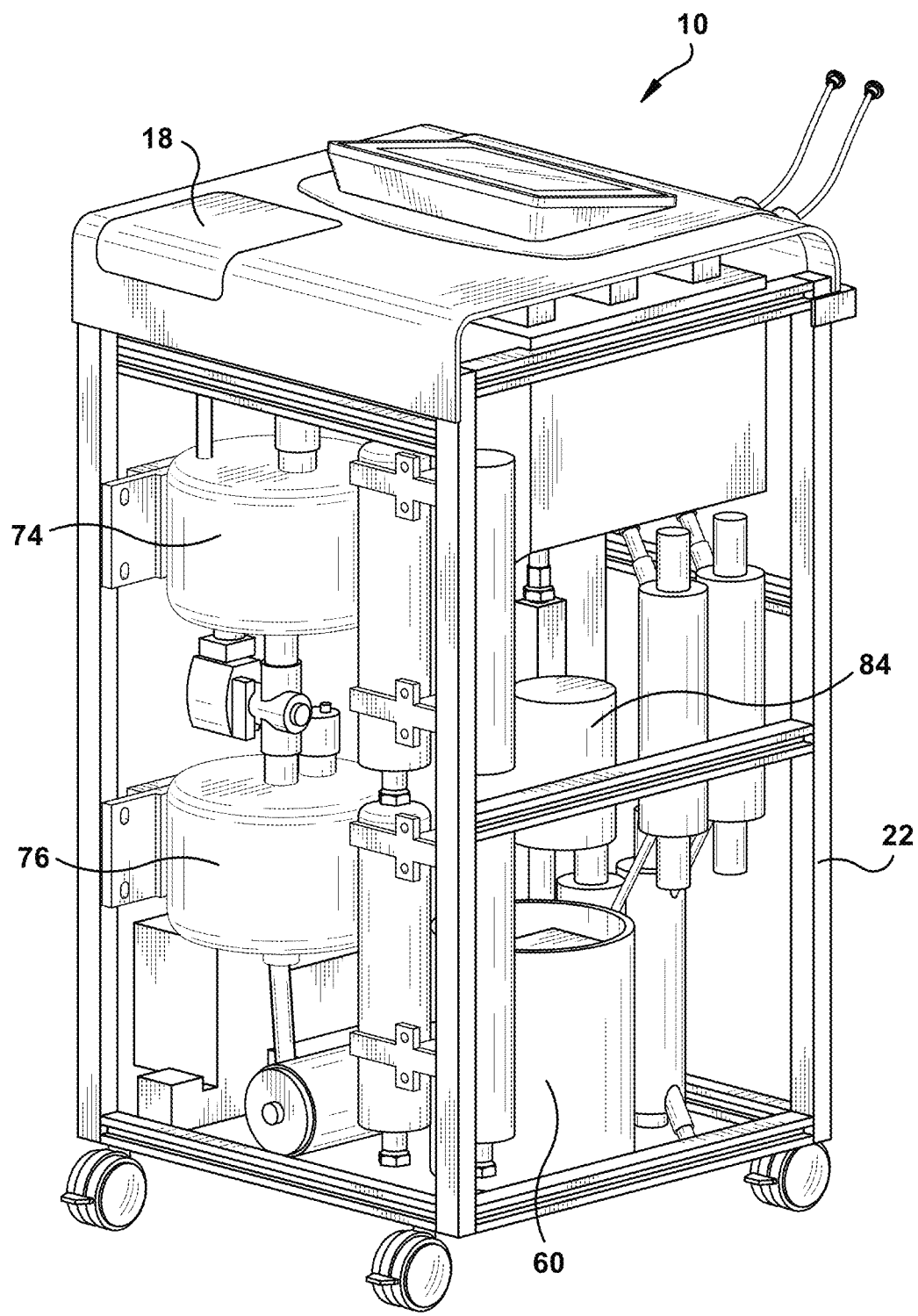
FIG. 6 is a rear perspective view of the in FIG. 5.

A connection port 20 can be provided on the housing 12. The connection port 20 can be configured to connect the dispensing mechanism 90 to the housing 12. An intake port 21 can also be provided on the housing 12. The intake port 21 can be configured to allow the system 10 to be filled with a fluid, such as water. The housing 12 can be provided with an electrical connection (not shown) for providing power to the system 10 (e.g., no more than 20 amperes at 115 volts alternating current or 10 amperes at 220 volts single phase). The system 10 can also include a frame 22 (FIGS. 5-6) to which the housing 12 is mounted. The frame 22 can be manufactured out of a single material or a combination of materials, such as metals, plastics, or a combination thereof.

A user interface/control module 23 can be associated with the housing 12. The user interface/control module 23 can be in electrical communication with the controller 14. The user interface/control module 23 may include various electrical components (e.g. micro processor, memory) configured to control certain operational characteristics of the system 10, such as fluid flow rate, fluid temperature, and/or solute concentration. The user interface/control module 23 may be provided with software programs. In one aspect, the user interface/control module 23 can comprise a touch screen that enables an operator to interact with the software program(s) and control operational characteristics of the system 10.

The fluid reservoir 40 can be directly or indirectly attached to the frame 22. The fluid reservoir 40 can be configured to hold a fluid (e.g., non-sterile water) prior to sterilization and/or purification by the system 10. In one aspect, the fluid reservoir 40 is capable of holding at least 15 L of fluid. It will be appreciated that other sized fluid reservoirs may be used. The fluid reservoir 40 is fluidly coupled to the intake port 21 by a first fluid conduit 24a. In general, the first fluid conduit 24a can be a tube having a substantially circular cross-section. The first fluid conduit 24a can have a rigid, semi-rigid, or flexible configuration, and be made of one material or a combination of materials. A second fluid conduit 24b can fluidly couple the fluid reservoir 40 to a water pump 42, which is attached to the frame 22. In one aspect, the water pump 42 is a ⅛ horsepower diaphragm-type pump. It will be appreciated that any other suitable pump may be used.

Figure 3:
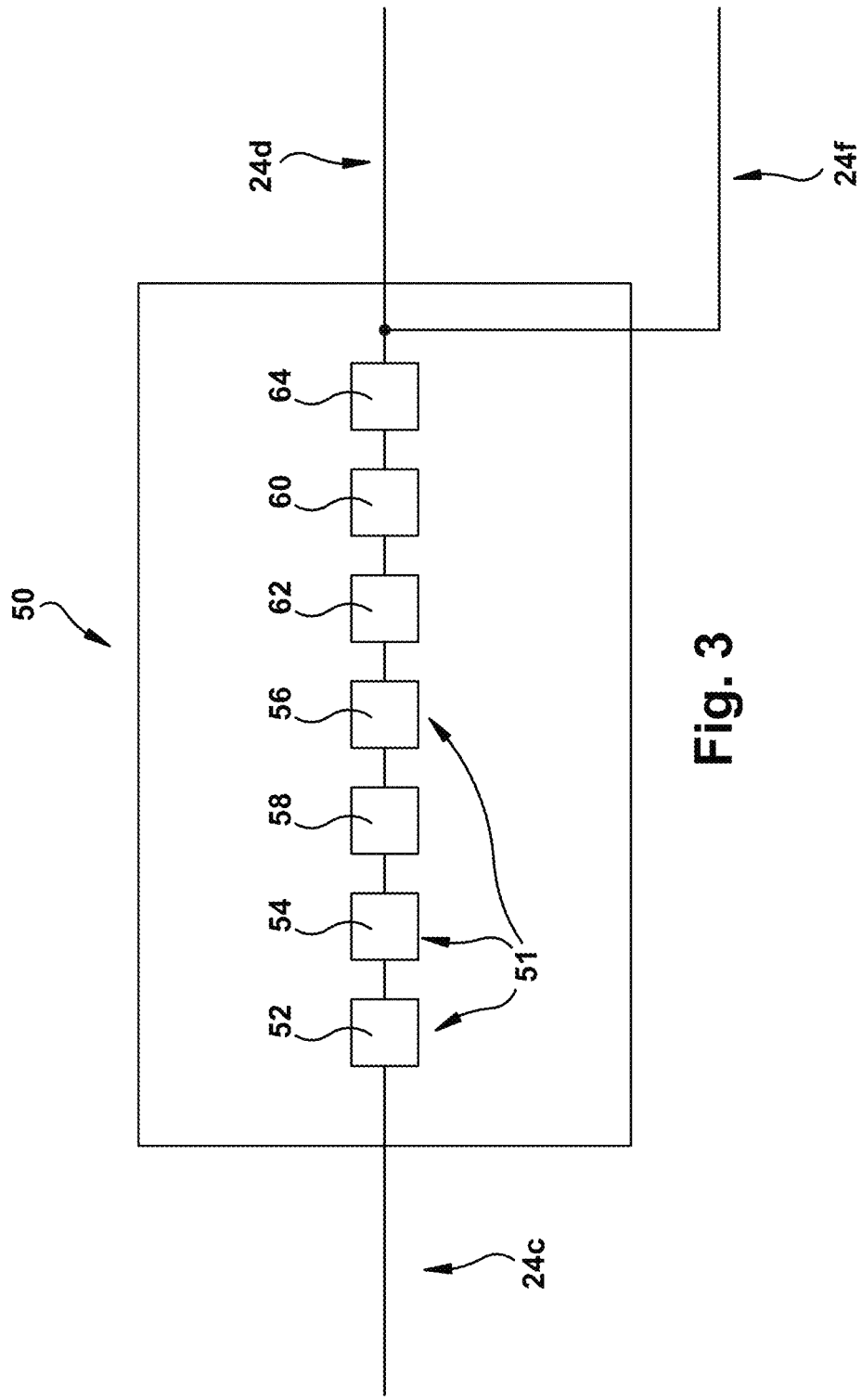
FIG. 3 is a schematic illustration of a sterilization mechanism comprising the system in FIG. 1.
Figure 4:
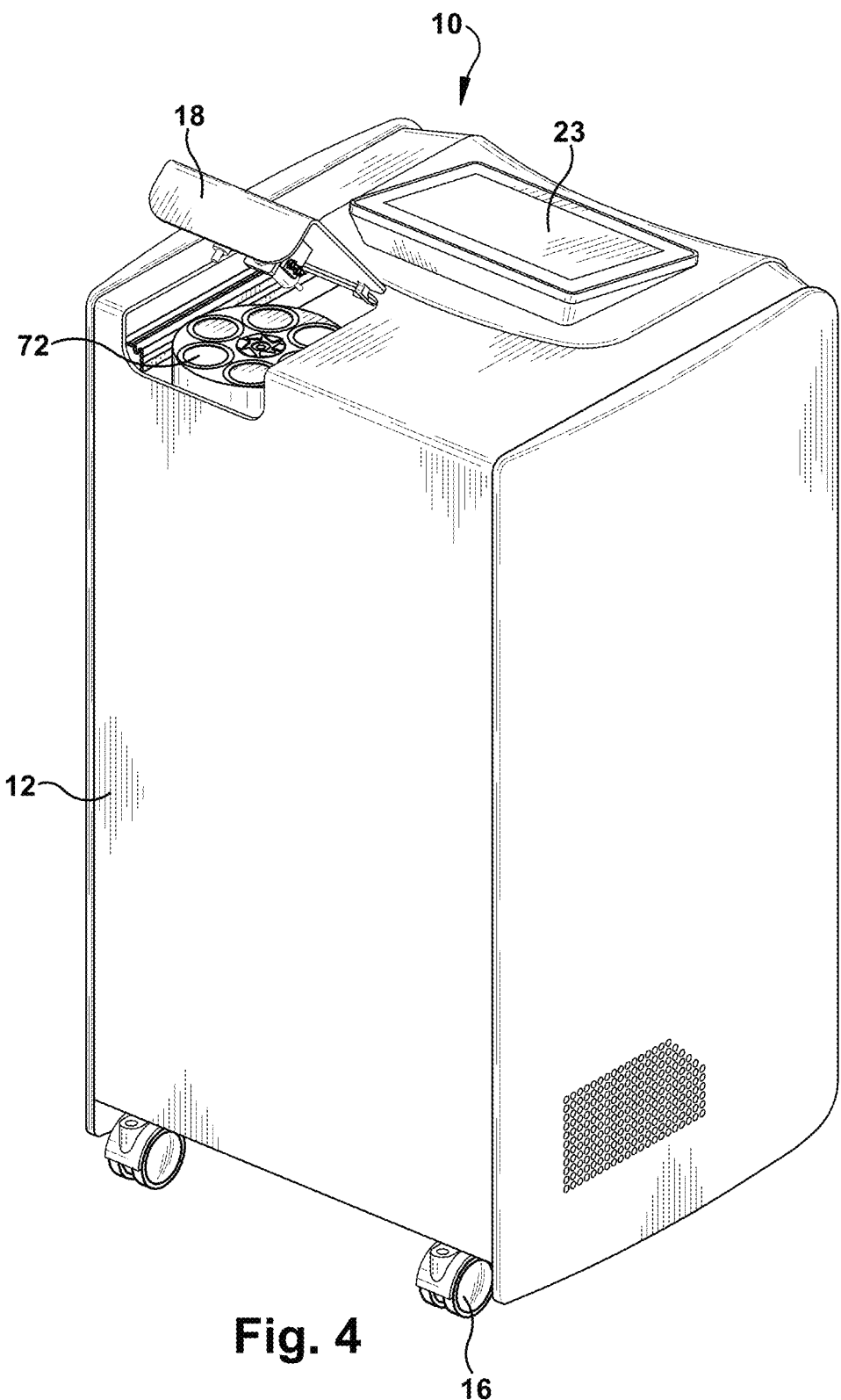
FIG. 4 is a perspective view of the system in FIG. 1 showing a multi-bore solute cartridge carrier.

The sterilization and/or purification mechanism 50 can be directly or indirectly attached to the frame 22 and fluidly coupled to the water pump 42 by a third fluid conduit 24c (FIG. 3). The sterilization and/or purification mechanism 50 can include any number of components and arrangements configured to remove impurities from, and sterilize, the fluid contained in the fluid reservoir 40. The sterilization and/or purification mechanism 50 can include at least one filter 51, at least one mixed bed resin tank 58, at least one continuous electrodeionization module 60, and at least one ultra-violet module 62. In one example, the sterilization and/or purification mechanism 50 can include three filters 52, 54, 56, one mixed bed resin tank 58, one continuous electrodeionization module 60, and two ultra-violet modules 62, 64.

In some instances, the filters 51 comprising the sterilization and/or purification mechanism 50 can include a prefilter 52 designed to remove impurities larger than about 5 µm, a carbon filter 54 designed to remove impurities larger than about 1 µm, and a fines filter 56 designed to remove impurities larger than about 1 µm. The mixed bed resin tank 58 can include anion and cation resins configured to remove poisonous and heavy metals from the fluid. The continuous electrodeionization module 60 can be configured to substantially deionize the fluid. The ultra-violet modules 62, 64 can be configured to emit energy at about 254 nm to disinfect the fluid and destroy ozone in the fluid. The ultra-violet modules 62, 64 can further be configured to emit energy at about 185 nm to destroy and decompose organic molecules in the fluid.

It will be appreciated that the components comprising the sterilization and/or purification mechanism 50 can be configured to achieve various purification and sterilization goals. For example, the number of filters can be increased or decreased. Additionally, the selectivity of the filters can be changed to remove impurities larger than 5 µm or smaller than 1 µm. In another example, the number of ultra-violet modules can be increased or decreased, as can the emitted wavelength of each lamp. As a further example, a capacitive deionization module can be substituted for the continuous electrodeionization module 60.

The solution production mechanism 70 can be configured to mix the sterilized and/or purified fluid produced by the sterilization and/or purification mechanism 50 with a solute to create a sterilized and/or purified solution. The solution production mechanism 70 can be directly or indirectly attached to the frame 22. The solution production mechanism 70 can be fluidly coupled to the sterilization and/or purification mechanism 50 by a fourth fluid conduit 24d. In one aspect, the solution production mechanism 70 can include a multi-bore solute cartridge carrier 72, at least one mix tank 74, and at least one solution reservoir tank 76. One example of the multi-bore solute cartridge carrier 72 is disclosed in U.S. Prov. Patent Appln. Ser. No. 62/132,589, filed Mar. 13, 2015 (hereinafter, "the '589 application"). The mix tank 74 can be configured to ensure that the sterilized and/or purified solution is adequately mixed to form a desired solution. For example, the mix tank 74 can include agitators that agitate the sterilized and/or purified fluid to ensure the solute is completely dissolved therein.

The solution reservoir tank 76 can be configured to hold the resultant sterilized and/or purified solution until it is requested by an operator. It will be appreciated that the solution production mechanism 70 can be modified to alter various performance characteristics of the system 10. For example, the size of the solution reservoir tank 76 may be increased or decreased to allow the system 10 to hold a greater or lesser amount of purified and sterilized solution that is ready for on-demand use.

A solution bypass line 80 can be provided in parallel flow with the solution production mechanism 70. The solution bypass line 80 can include a bypass line filter that is fluidly 82 coupled to the sterilization and/or purification mechanism 50 by a sixth fluid conduit 24f. In one aspect, the bypass line filter 82 is designed to remove impurities larger than 0.1 µm.

A temperature regulating mechanism 84 configured to heat and/or cool the fluid can be directly or indirectly attached to the frame 22. The temperature regulating mechanism 84 can be fluidly coupled to the solution production mechanism 70 and the solution bypass line 80 by a seventh fluid conduit 24g. A final filter 78 can be disposed between the solution production mechanism 70 and the temperature regulating mechanism 84. The final filter 78 can be fluidly coupled to the solution production mechanism 70 and the temperature regulating mechanism by a fifth fluid conduit 24e, and the seventh fluid conduit 24g, respectively. In one aspect, the first final filter 78 is designed to remove impurities larger than about 0.1 µm.

The temperature regulating mechanism 84 can additionally be configured to direct fluid that flows through the solution production mechanism 70 along a first fluid route 25a and/or to direct fluid that passes through the solution bypass line 80 along a second fluid route 25b. In one aspect, the temperature regulating mechanism 84 can include resistive heaters to heat the fluid and/or a compressed gas refrigeration cycle to cool the fluid to regulate the fluid temperature to about 45° C. such that the fluid is close to body temperature once the fluid reaches the patient. It will be appreciated that any other suitable heating and cooling mechanism may be used, and that the temperature regulating mechanism 84 can be configured to regulate the temperature of the fluid to any desired temperature. An eighth fluid conduit 24h can fluidly couple the temperature regulating mechanism 84 to the connection port 20. The eighth fluid conduit 24h can be configured to maintain the separate first and second fluid routes 25a, 25b.

Figure 7:
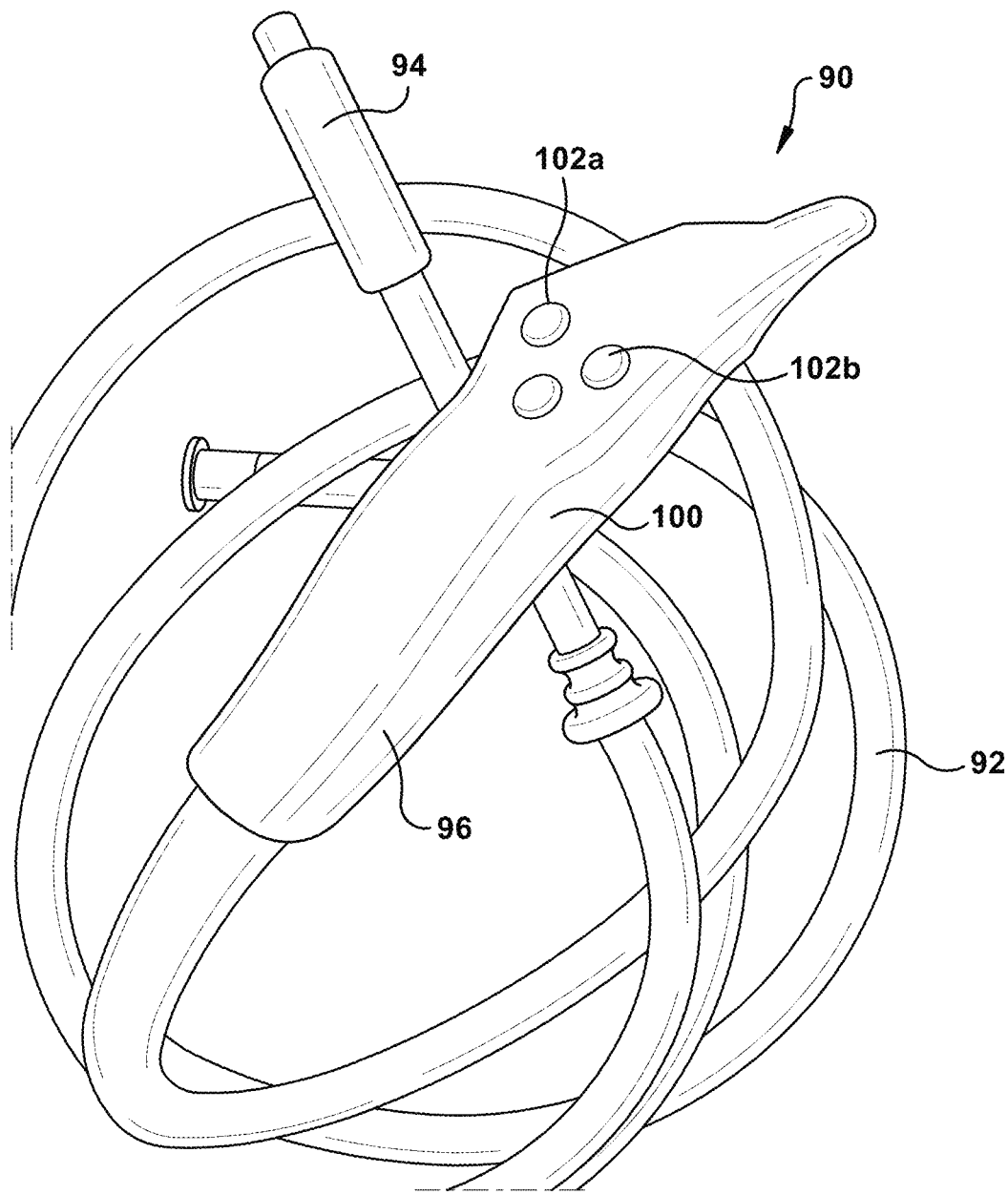
FIG. 7 is an image of a dispensing mechanism comprising the system in FIG. 1.

Referring to FIG. 7, the system 10 can include a dispensing mechanism 90 adapted for connection with the connection port 20. In one aspect, the dispensing mechanism 90 can include a tubular portion 92, a male connection member 94 disposed at a first end of the tubular portion 92, and a dispensing member 96 disposed at a second end of the tubular portion 92 opposite the first end. The male connection member 94 can include a first fluid path 25*c* and a second fluid path 25*d*, and can be configured to be inserted into the connection port 20. When the male connection member 94 is inserted into the connection port 20, the first and second fluid paths 25*c*, 25*d* of the male connection member 94 can be fluidly coupled to the first and second fluid routes 25*a*, 25*b*, respectively, of the eighth fluid conduit 24*h*.

The tubular portion 92 of the male connection member 94 can include a flexible hose configured to separately maintain the first and second fluid paths 25*c*, 25*d*. The tubular portion 92 can include a first tubeset filter 98 and a second tubeset filter 99 respectively disposed in the first fluid path 25*c* and the second fluid path 25*d*. In one aspect, the first and second tubeset filters 98, 99 can be designed to remove impurities larger than about 0.05 μm. It will be appreciated that any other suitable filter can be used.

The dispensing member 96 can include an ergonomic handle 100. A first end of the handle 100 can be configured for connection with the second end of the tubular portion 92. A second end of the handle 100 opposite the first end can be configured to dispense the purified and sterilized fluid and/or solution to a desired area. In one aspect, the handle 100 can be configured to combine the first and second fluid paths 25*c*, 25*d* into a single fluid path that flows out of the second end of the handle 100. It will be appreciated that the handle can be configured to keep the first and second fluid paths 25*c*, 25*d* separate.

The handle 100 can comprise at least one dispensing button 102*a-c*. In one aspect, the handle 100 can include a first dispensing button 102*a* associated with the first fluid path 25*c*, and a second dispensing button 102*b* associated with the second fluid path 25*d*. It will be appreciated that the handle 100 may be provided with a fewer or greater number of buttons to customize the level of fluid control afforded to an operator of the system 10.

Methods

Figure 8:
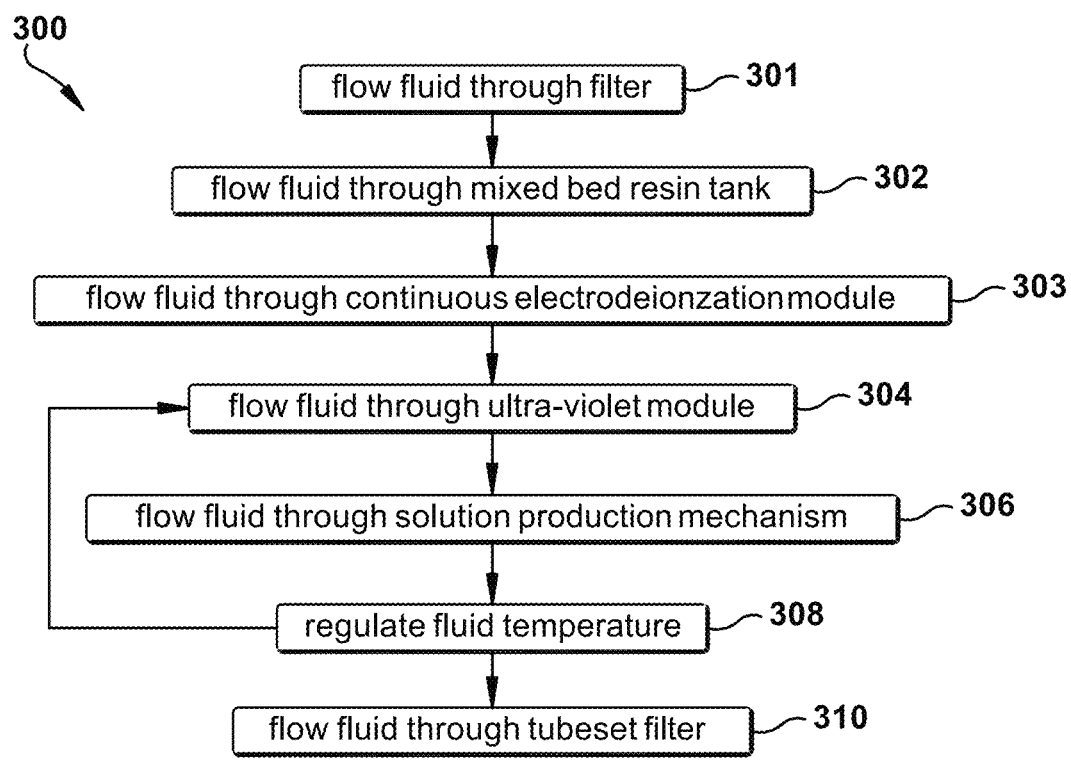
FIG. 8 is a process flow diagram illustrating a method for providing a sterile and/or purified fluid according to another aspect of the present disclosure.

Another aspect of the present disclosure can include a method 300 (FIG. 8) for providing a sterile and/or purified fluid and/or solution. First, an operator can fill the fluid reservoir 40 with a desired fluid, such as water. In one example, the operator can fill the fluid reservoir 40 by attaching a filling hose to the intake port 21. It will be appreciated that other methods can be used to fill the fluid reservoir 40. For example, the housing 12 can be provided with an access port that allows access to the fluid reservoir 40. Alternatively, an operator can transfer water directly from a fluid carrying vessel to the fluid reservoir 40 via the access port.

Next, the operator can connect the system 10 with a power source via the electrical connection provided on the housing 12. The operator can also ensure the dispensing mechanism 90 is connected with the connection port 20. The operator can then interface with the system 10 via the user interface/control module 23 to set desired parameters relating to the fluid and/or solution that is to be dispensed. In one example, the user interface/control module 23 can enable the operator to control the temperature and flow rate of the dispensed fluid and/or solution. It will be appreciated that the user interface/control module 23 can be customized to control other operational characteristics of the system 10, such as the concentration of the dispensed fluid and/or solution. The user interface/control module 23 can also be configured to provide information relating to the condition of various characteristics of the system 10, such as the amount of fluid remaining in the fluid reservoir 40.

Once the parameter(s) of the fluid and/or solution to be dispensed is/are programmed, the water pump 42 is operated to pump water from the fluid reservoir 40 to the sterilization mechanism 50 via the second and third fluid conduits 24*b*, 24*c*. At Steps 301-304, the water is purified and sterilized as it passes through the sterilization mechanism 50. For example, purification and sterilization of the water can be achieved by passing the water through the pre-filter 52, the carbon filter 54, the mixed bed resin tank 58, the fines filter 56, the first ultraviolet module 62, the continuous electro-deionization module 60 and the second ultraviolet module 64.

Next, the water can be directed into one of two separate fluid paths. A first fluid path carries the water to the solution production mechanism 70. A second fluid path carries the water to the bypass line 80. If the water is directed to the solution production mechanism 70 (Step 306), the multiple-bore solute cartridge carrier 72 mixes the sterilized and/or purified water with a solute to create a sterilized and/or purified solution as discussed in the '589 application. The solution can then pass into the mix tank 74, where the solution can be further agitated. The solution can next pass into the solution reservoir tank 76 where the solution remains until the operator makes a request for its delivery.

The operator can request that the solution be dispensed by depressing the first button 102*a* on the handle 100. When the first button 102*a* is depressed, the solution can flow through the final filter 78 into the temperature regulating mechanism 84. At Step 308, the temperature regulating mechanism 84 can heat or cool the fluid and/or solution as desired. The fluid and/or solution can then flow from temperature regulating mechanism 84 through the connection port 20, via the dispensing mechanism 90 while passing through the first tubeset filter 98 (Step 310). The solution can be dispensed at a rate of at least 1 L/min (e.g., about 1-2 L/minute, about 2-3 L/minute, about 3-4 L/minute, about 4-5 L/minute, about 5-6 L/minute, about 6-7 L/minute, about 7-8 L/minute, about 8-9 L/minute, about 9-10 L/minute, or greater than 10 L/minute, such as 10-20 L/minute, 20-30 L/minute, 30-40 L/minute, or more), which advantageously allows the operator to thoroughly and quickly irrigate a worksite (e.g., cleaning tissue during surgery in an operating room). In one example, the solution can be dispensed at a rate of 10 L/minute.

The operator can additionally or alternatively request that a sterilized and/or purified fluid (e.g., free of solute) be dispensed by depressing the second button 102*b* on the handle 100. When the second button 102*b* is depressed, the fluid can be directed along the second fluid path through the bypass line 80. The fluid can then flow through the second final filter 82 and the connection port 20 via the dispensing mechanism 90 while passing through the second tubeset filter 99 (Step 310). The fluid can be dispensed at a rate of at least 1 L/minute (e.g., 10 L/minute), which advantageously allows the operator to thoroughly and quickly irrigate a worksite (e.g., cleaning tissue during surgery). It will be appreciated that the system 10 can be configured to dispense a sterilized and/or purified solution or fluid at a rate of less than 1 L/minute (e.g. about 1-0.9 L/minute, about 0.9-0.8 L/minute, about 0.8-0.7 L/minute, about 0.7-0.6 L/minute, about 0.6-0.5 L/minute, about 0.5-0.4 L/minute, about 0.4-0.3 L/minute, about 0.3-0.2 L/minute, about 0.2-0.1 L/minute, or 0.1 L/minute or less). For instance, the system 10 can be configured to dispense a sterilized and/or purified solution or fluid at a rate of 0.8 L/minute.

From the above description of the present disclosure, those skilled in the art will perceive improvements, changes and modifications. For example, the system 10 can be configured to deliver pulsatile flow. Additionally, the system can include a sensing mechanism (not shown) in electrical communication with the controller 14 and/or the user interface/control module 23. The sensing mechanism can sense characteristics of the fluid and or solution, such as flow rate, pH level, pressure, salinity, etc. All patents and patent applications identified herein are hereby incorporated by reference for all purposes. Such improvements, changes, and modifications are within the skill of the art and are intended to be covered by the appended claims.

The following is claimed:

1. A system for on-demand delivery of a sterile fluid, comprising:
   a housing;
   at least one fluid reservoir in the housing and configured to hold a fluid;
   a sterilization and/or purification mechanism in the housing and in fluid communication with the at least one fluid reservoir, the sterilization and/or purification mechanism being configured to sterilize the fluid, components of the sterilization and/or purification mechanism that sterilize the fluid include:
      a pre-filter configured to remove impurities larger than about 5 µm from the fluid,
      a carbon filter downstream of the pre-filter and configured to remove the impurities larger than about 1 µm from the fluid,
      a mixed bed resin tank downstream of the carbon filter and configured to remove poisonous and heavy metals from the fluid,
      a fines filter downstream of the mixed bed resin tank and configured to remove the impurities larger than about 1 µm from the fluid,
      a first ultra-violet module downstream of the fines filter and configured to disinfect the fluid and destroy ozone in the fluid or to destroy and decompose organic molecules in the fluid,
      an electrodeionization module downstream of the first ultra-violet module and configured to substantially deionize the fluid, and
      a second ultra-violet module downstream of the electrodeionization module and configured to disinfect the fluid and destroy the ozone in the fluid or to destroy and decompose the organic molecules in the fluid; and
   a dispensing mechanism in fluid communication with the sterilization and/or purification mechanism and configured to dispense the sterile fluid;
   wherein the system is configured to deliver the sterile fluid to a desired area outside of the system after a request is made.

2. The system of claim 1, further comprising a controller associated with one or more of the at least one fluid reservoir, the sterilization and/or purification mechanism, and the dispensing mechanism, the controller being configured to modulate at least one operating characteristic of the system.

3. The system of claim 1, wherein the first and second ultra-violet modules are configured to emit energy at about 254 nm to disinfect the fluid and destroy the ozone in the fluid or emit the energy at about 185 nm to destroy and decompose the organic molecules in the fluid.

4. The system of claim 1, further comprising:
   a solution production mechanism in the housing, the solution production mechanism being separate from and in fluid communication with the sterilization and/or purification mechanism and the dispensing mechanism, the solution production mechanism being configured to receive the sterile fluid from the sterilization and/or purification mechanism, the solution production mechanism being configured to selectively mix a solute with the received sterile fluid to produce a sterile solution;
   wherein the dispensing mechanism is configured to dispense one or more of the sterile fluid and the sterile solution; and
   wherein the system is configured to deliver one or more of the sterile fluid and the sterile solution to the desired area outside of the system after the request is made.

5. The system of claim 4, wherein the solution production mechanism includes a multi-bore solute cartridge carrier received in the housing, the multi-bore solute cartridge carrier including:
   a rotary housing having one or more bores, each bore extending along a central axis between a filling end and a draining end, and
   one or more solute cartridges received in the one or more bores, each solute cartridge including a frame, a filter supported by the frame, and a solute contained therein, each filter substantially extending perpendicular with respect to an associated central axis so that the sterile fluid, when flowing from the filling end to the draining end of an associated bore, flows through the filter,
the solution production mechanism being configured to selectively flow the received sterile fluid through the one or more solute cartridges to mix the received sterile fluid with the solute to produce the sterile solution.

6. The system of claim 4, further comprising a temperature regulating mechanism in fluid communication with one or more of the solution production mechanism and the sterilization and/or purification mechanism, the temperature regulating mechanism is configured to heat or cool one or more of the sterile fluid and the sterile solution.

7. The system of claim 4, further comprising a solution bypass line in fluid communication with the sterilization and/or purification mechanism and the dispensing mechanism, the solution bypass line providing a fluid path from the sterilization and/or purification mechanism to the dispensing mechanism that bypasses the solution production mechanism for the dispensing of the sterile fluid to the desired area outside of the system after the request is made.

8. The system of claim 1, wherein the system is configured to deliver the sterile fluid to the desired area outside of the system within about ten seconds after the request is made.

* * * * *